United States Patent
Guo et al.

(10) Patent No.: US 11,674,161 B2
(45) Date of Patent: Jun. 13, 2023

(54) MODIFIED MONOOXYGENASES FOR THE MANUFACTURE OF HYDROXYLATED HYDROCARBONS

(71) Applicant: Covestro Intellectual Property GmbH & Co. KG, Leverkusen (DE)

(72) Inventors: Ruijing Guo, Shanghai (CN); Jen-Chieh Lin, Singapur (SG); Sha Tao, Nanjing (CN); Ying Qian, Nanjing (CN); Chenggang Qiu, Nanjing (CN); Kequan Chen, Nanjing (CN); Kang Li, Nanjing (CN)

(73) Assignee: Covestro Intellectual Property GmbH & Co. KG, Leverkusen (DE)

( * ) Notice: Subject to any disclaimer, the term of this patent is extended or adjusted under 35 U.S.C. 154(b) by 0 days.

(21) Appl. No.: 17/607,922

(22) PCT Filed: Jun. 18, 2020

(86) PCT No.: PCT/EP2020/066892
§ 371 (c)(1),
(2) Date: Nov. 1, 2021

(87) PCT Pub. No.: WO2020/260119
PCT Pub. Date: Dec. 30, 2020

(65) Prior Publication Data
US 2022/0220513 A1    Jul. 14, 2022

(30) Foreign Application Priority Data

Jun. 27, 2019 (WO) ................ PCT/CN2019/093275
Jun. 27, 2019 (WO) ................ PCT/CN2019/093326
Aug. 16, 2019 (EP) ..................................... 19192042
Aug. 16, 2019 (EP) ..................................... 19192044

(51) Int. Cl.
*C12N 9/00* (2006.01)
*C12P 7/22* (2006.01)
*C12N 9/02* (2006.01)
*C12P 17/06* (2006.01)

(52) U.S. Cl.
CPC .............. *C12P 7/22* (2013.01); *C12N 9/0077* (2013.01); *C12N 9/0079* (2013.01); *C12P 17/06* (2013.01); *C12Y 114/15004* (2013.01)

(58) Field of Classification Search
CPC .. C12N 9/0071; C12N 9/0077; C12N 9/0008; C12N 9/0079; C12N 9/0004; C12N 9/0042; C12P 7/04; C12P 7/22; C12P 7/02; C12Y 114/14001; C12Y 114/15; C12Y 114/15003; C12Y 114/15006
USPC .......................... 435/189, 157, 252.3, 320.1
See application file for complete search history.

(56) References Cited

PUBLICATIONS

Liu, L. et al, Cloning, expression, and characterization of a self-sufficient cytochrome P450 monooxygenase from Rhodococcus ruber DSM 44319, Applied Microbiology and Biotechnology, vol. 72, No. 5, Apr. 11, 2006, pp. 876-882, XP037057208.

Tao, S. et al., "Engineering substrate recognition sites of cytochrome P450 monooxygenase CYP116B3 from Rhodococcus ruber for enhanced regiospecific naphtalene hydroxylation", Molecular Catalysis; vol. 493, pp. 1-6; Jul. 7, 2020, XP055729749.

International Search Report, PCT/EP2020/066892, dated Oct. 22, 2020, Authorized officer: Ulrike Fuchs.

*Primary Examiner* — Robert B Mondesi
*Assistant Examiner* — Mohammad Y Meah
(74) *Attorney, Agent, or Firm* — The Webb Law Firm

(57) ABSTRACT

The present invention relates to novel monooxygenases which are useful in the hydroxylation of aromatic hydrocarbons. They are particularly useful for the production of 1-naththol and 7-hydroxycoumarin from naphthol and 7-Ethoxycoumarin, respectively.

11 Claims, No Drawings
Specification includes a Sequence Listing.

SEQUENCE LISTING

```
<160> NUMBER OF SEQ ID NOS: 4

<210> SEQ ID NO 1
<211> LENGTH: 771
<212> TYPE: PRT
<213> ORGANISM: Rhodococcus ruber

<400> SEQUENCE: 1

Met Ser Ala Ser Val Pro Ala Ser Ala Cys Pro Val Asp His Ala Ala
1               5                   10                  15

Leu Ala Gly Gly Cys Pro Val Ser Thr Asn Ala Ala Ala Phe Asp Pro
                20                  25                  30

Phe Gly Pro Ala Tyr Gln Ala Asp Pro Ala Glu Ser Leu Arg Trp Ser
            35                  40                  45

Arg Asp Glu Glu Pro Val Phe Tyr Ser Pro Glu Leu Gly Tyr Trp Val
        50                  55                  60

Val Thr Arg Tyr Glu Asp Val Lys Ala Val Phe Arg Asp Asn Leu Val
65                  70                  75                  80

Phe Ser Pro Ala Ile Ala Leu Glu Lys Ile Thr Pro Val Ser Glu Glu
                85                  90                  95

Ala Thr Ala Thr Leu Ala Arg Tyr Asp Tyr Ala Met Ala Arg Thr Leu
            100                 105                 110

Val Asn Glu Asp Glu Pro Ala His Met Pro Arg Arg Arg Ala Leu Met
        115                 120                 125

Asp Pro Phe Thr Pro Lys Glu Leu Ala His His Glu Ala Met Val Arg
    130                 135                 140

Arg Leu Thr Arg Glu Tyr Val Asp Arg Phe Val Glu Ser Gly Lys Ala
145                 150                 155                 160

Asp Leu Val Asp Glu Met Leu Trp Glu Val Pro Leu Thr Val Ala Leu
                165                 170                 175

His Phe Leu Gly Val Pro Glu Glu Asp Met Ala Thr Met Arg Lys Tyr
            180                 185                 190
```

```
Ser Ile Ala His Thr Val Asn Thr Trp Gly Arg Pro Ala Pro Glu Glu
            195                 200                 205

Gln Val Ala Val Ala Glu Ala Val Gly Arg Phe Trp Gln Tyr Ala Gly
210                 215                 220

Thr Val Leu Glu Lys Met Arg Gln Asp Pro Ser Gly His Gly Trp Met
225                 230                 235                 240

Pro Tyr Gly Ile Arg Met Gln Gln Gln Met Pro Asp Val Val Thr Asp
                245                 250                 255

Ser Tyr Leu His Ser Met Met Met Ala Gly Ile Val Ala Ala His Glu
            260                 265                 270

Thr Thr Ala Asn Ala Ser Ala Asn Ala Phe Lys Leu Leu Leu Glu Asn
            275                 280                 285

Arg Pro Val Trp Glu Glu Ile Cys Ala Asp Pro Ser Leu Ile Pro Asn
            290                 295                 300

Ala Val Glu Glu Cys Leu Arg His Ser Gly Ser Val Ala Ala Trp Arg
305                 310                 315                 320

Arg Val Ala Thr Thr Asp Thr Arg Ile Gly Asp Val Asp Ile Pro Ala
                325                 330                 335

Gly Ala Lys Leu Leu Val Val Asn Ala Ser Ala Asn His Asp Glu Arg
            340                 345                 350

His Phe Asp Arg Pro Asp Glu Phe Asp Ile Arg Arg Pro Asn Ser Ser
            355                 360                 365

Asp His Leu Thr Phe Gly Tyr Gly Ser His Gln Cys Met Gly Lys Asn
            370                 375                 380

Leu Ala Arg Met Glu Met Gln Ile Phe Leu Glu Leu Thr Thr Arg
385                 390                 395                 400

Leu Pro His Met Glu Leu Val Pro Asp Gln Glu Phe Thr Tyr Leu Pro
                405                 410                 415

Asn Thr Ser Phe Arg Gly Pro Asp His Val Trp Val Gln Trp Asp Pro
                420                 425                 430

Gln Ala Asn Pro Glu Arg Thr Asp Pro Ala Val Leu Gln Arg Gln His
            435                 440                 445

Pro Val Thr Ile Gly Glu Pro Ser Thr Arg Ser Val Ser Arg Thr Val
            450                 455                 460

Thr Val Glu Arg Leu Asp Arg Ile Val Asp Asp Val Leu Arg Val Val
465                 470                 475                 480

Leu Arg Ala Pro Ala Gly Asn Ala Leu Pro Ala Trp Thr Pro Gly Ala
                485                 490                 495

His Ile Asp Val Asp Leu Gly Ala Leu Ser Arg Gln Tyr Ser Leu Cys
            500                 505                 510

Gly Ala Pro Asp Ala Pro Thr Tyr Glu Ile Ala Val Leu Leu Asp Pro
            515                 520                 525

Glu Ser Arg Gly Gly Ser Arg Tyr Val His Glu Gln Leu Arg Val Gly
            530                 535                 540

Gly Ser Leu Arg Ile Arg Gly Pro Arg Asn His Phe Ala Leu Asp Pro
545                 550                 555                 560

Asp Ala Glu His Tyr Val Phe Val Ala Gly Gly Ile Gly Ile Thr Pro
                565                 570                 575

Val Leu Ala Met Ala Asp His Ala Arg Ala Arg Gly Trp Ser Tyr Glu
                580                 585                 590

Leu His Tyr Cys Gly Arg Asn Arg Ser Gly Met Ala Tyr Leu Glu Arg
            595                 600                 605
```

```
Val Ala Gly His Gly Asp Arg Ala Ala Leu His Val Ser Ala Glu Gly
610                 615                 620

Thr Arg Val Asp Leu Ala Ala Leu Leu Ala Thr Pro Val Ser Gly Thr
625                 630                 635                 640

Gln Ile Tyr Ala Cys Gly Pro Gly Arg Leu Leu Ala Gly Leu Glu Asp
                645                 650                 655

Ala Ser Arg His Trp Pro Asp Gly Ala Leu His Val Glu His Phe Thr
                660                 665                 670

Ser Ser Leu Thr Ala Leu Asp Pro Asp Val Glu His Ala Phe Asp Leu
            675                 680                 685

Asp Leu Arg Asp Ser Gly Leu Thr Val Arg Val Glu Pro Thr Gln Thr
690                 695                 700

Val Leu Asp Ala Leu Arg Ala Asn Asn Ile Asp Val Pro Ser Asp Cys
705                 710                 715                 720

Glu Glu Gly Leu Cys Gly Ser Cys Glu Val Thr Val Leu Glu Gly Glu
                725                 730                 735

Val Asp His Arg Asp Thr Val Leu Thr Lys Ala Glu Arg Ala Ala Asn
                740                 745                 750

Arg Gln Met Met Thr Cys Cys Ser Arg Ala Cys Gly Asp Arg Leu Thr
755                 760                 765

Leu Arg Leu
770

<210> SEQ ID NO 2
<211> LENGTH: 7672
<212> TYPE: DNA
<213> ORGANISM: Artificial Sequence
<220> FEATURE:
<223> OTHER INFORMATION: Expression construct

<400> SEQUENCE: 2
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccttttagg     180 gttccgattt agtgctttac ggcacctcga ccccaaaaaa cttgattagg gtgatggttc     240
acgtagtggg ccatcgccct gatagacggt ttttcgccct tgacgttgg agtccacgtt     300 ctttaatagt ggactcttgt tccaaactgg aacaacactc aacccatct cggtctattc     360 ttttgattta agggattt tgccgatttc ggcctattgg ttaaaaaatg agctgattta      420
acaaaaattt aacgcgaatt ttaacaaaat attaacgttt acaatttcag gtggcacttt     480
tcggggaaat gtgcgcggaa cccctatttg tttattttc taaatacatt caaatatgta      540
tccgctcatg aattaattct tagaaaaact catcgagcat caaatgaaac tgcaattttat    600 tcatatcagg attatcaata ccatattttt gaaaagccg tttctgtaat gaaggagaaa     660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa agtttatgc atttctttcc    840 agacttgttc aacaggccag ccattacgct cgtcatcaaa atcactcgca tcaaccaaac    900
cgttattcat tcgtgattgc gcctgagcga cgaaatac gcgatcgctg ttaaaaggac      960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
```

```
tggtgagtaa ccatgcatca tcaggagtac ggataaaatg cttgatggtc ggaagaggca    1140
taaattccgt cagccagttt agtctgacca tctcatctgt aacatcattg caacgctac     1200 ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actctttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccggggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcaggggggg cggagcctat ggaaaaacgc cagcaacgcg    2100
gcctttttac ggttcctggc cttttgctgg ccttttgctc acatgttctt cctgcgtta    2160 tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt ttcctgtttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
```

```
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg cgcgcattg    3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa agacaccgg    4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg cgatataggc gccagcaac  cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa cttaagaag  gagatatacc atgggcagca gccatcatca tcatcatcac   5100
agcagcggcc tggtgccgcg cggcagccat atgctagca tgactggtgg acagcaaatg    5160
ggtcgcggat ccgaattcat gagtgcatca gttccggcgt cggcgtgtcc cgtcgatcac   5220
gcggccctgg ccggcggctg tccggtgtcg acgaacgccg cggcgttcga tccgttcggg   5280
cccgcgtacc aggccgatcc ggccgagtcg ctgcgctggt cccgcgacga ggagccggtg   5340
ttctacagcc ccgaactcgg ctactgggtg gtcacccgct acgaggatgt gaaggcggtg   5400
ttccgcgaca acctcgtgtt ctcaccggcc atcgccctcg agaagatcac cccggtctcc   5460
gaggaggcca ccgccaccct cgcccgctac gactacgcca tggcccggac cctcgtgaac   5520
gaggacgagc ccgccacat  gccgcgccgc cgcgcactca tggacccgtt caccccgaag   5580
gaactggcgc accacgaggc gatggtgcga cggctcacgc gcgaatacgt cgaccgcttc   5640
gtcgaatccg gcaaggccga cctggtggac gagatgctgt gggaggtacc gctcaccgtc   5700
gccctgcact tcctcggcgt gccggaggag gacatggcga cgatgcgcaa gtactcgatc   5760
gcccacaccg tgaacacctg gggccgcccc gcgcccgagg agcaggtcgc cgtcgccgag   5820
```

```
gcggtcggca ggttctggca gtacgcgggc acggtgctcg agaagatgcg ccaggacccc    5880
tcggggcacg gctggatgcc ctacgggatc cgcatgcagc agcagatgcc ggacgtcgtc    5940
accgactcct acctgcactc gatgatgatg gccggcatcg tcgccgcgca cgagaccacg    6000
gccaacgcgt ccgcgaacgc gttcaagctg ctgctcgaga accgcccggt gtgggaggag    6060
atctgcgcgg atccgtcgct gatccccaac gccgtcgagg agtgcctgcg ccactcggga    6120
tcggtcgcgg cgtggcgacg ggtggccacc accgacaccc gcatcggcga cgtcgacatc    6180
cccgccggcg caaagctgct cgtcgtcaac gcctccgcca accatgacga gcggcacttc    6240
gaccgtcccg acgagttcga catccggcgc ccgaactcga gcgaccacct caccttcggg    6300
tacggcagcc atcagtgcat gggcaagaac ctggcccgca tggagatgca gatcttcctc    6360
gaggaactga ccacgcggct tccccacatg gaactcgtac ccgatcagga gttcacctac    6420
ctgccgaaca cctcgttccg cggtcccgat cacgtgtggg tgcagtggga tccgcaggcg    6480
aaccccgagc gcaccgaccc ggccgtgctg caacggcagc atcccgtcac catcggcgag    6540
ccctccaccc ggtcggtgtc acgcaccgtc accgtcgagc gcctggaccg gatcgtcgac    6600
gacgtgctgc gcgtcgtcct acgggctcct gcaggaaatg cgttgcccgc gtggactcct    6660
ggcgcccaca tcgatgtcga cctcggtgcg ctgtcgcggc agtactccct gtgcggtgcg    6720
cccgacgcgc ccacctacga gatcgccgtt ctgctggacc ccgagagccg cggtggctcg    6780
cgctacgtcc acgaacagct ccgggtgggg ggatcgctcc ggattcgcgg gccccggaac    6840
cacttcgcgc tcgaccccga cgccgagcac tacgtgttcg tggccggcgg catcggcatc    6900 accccccgtcc tggccatggc cgaccacgcc cgcgcccggg ggtggagcta cgaactgcac    6960
tactgcggcc ggaaccgttc cgggatggcc tatctcgagc gggtcgccgg gcacggggac    7020
cgcgccgccc tgcacgtctc ggcggaaggc acccgggtcg acctcgccgc cctcctcgcg    7080
acgccggtgt ccggcaccca gatctacgcg tgcgggcccg acggctgctc gccggactc    7140 gaggacgcga gccggcactg gcccgacggt gcgctgcacg tcgagcactt caccctcgtcc    7200 ctcacggcac tcgacccgga cgtcgagcac gccttcgacc tcgacctgcg cgactcggga    7260
ctcaccgtgc gggtcgagcc cacccagacc gtcctcgacg cgttgcgcgc caacaacatc    7320
gacgtgccca gcgactgcga ggaaggcctc tgcggctcct gcgaggtcac cgtcctcgaa    7380
ggcgaggtcg accaccgcga caccgtgctc accaaggccg agcgggcggc gaaccggcag    7440
atgatgacct gctgctcgcg tgcctgcggc gaccgactga ccctccgact ctgaaagctt    7500
gcggccgcac tcgagcacca ccaccaccac cactgagatc cggctgctaa caaagcccga    7560
aaggaagctg agttggctgc tgccaccgct gagcaataac tagcataacc ccttggggcc    7620
tctaaacggg tcttgagggg ttttttgctg aaaggaggaa ctatatccgg at            7672
```

<210> SEQ ID NO 3  
<211> LENGTH: 31  
<212> TYPE: DNA  
<213> ORGANISM: Artificial Sequence  
<220> FEATURE:  
<223> OTHER INFORMATION: PCR primer

<400> SEQUENCE: 3
ctggaattca tgagtgcatc agttccggcg t                                    31

<210> SEQ ID NO 4  
<211> LENGTH: 27  
<212> TYPE: DNA  
<213> ORGANISM: Artificial Sequence

```
<220> FEATURE:
<223> OTHER INFORMATION: PCR primer

<400> SEQUENCE: 4
catcaagctt tcagagtcgc agggcca                                              27
```

MODIFIED MONOOXYGENASES FOR THE MANUFACTURE OF HYDROXYLATED HYDROCARBONS

CROSS-REFERENCE TO RELATED APPLICATION

This application is a national stage application under 35 U.S.C. § 371 of PCT/EP2020/066892, filed Jun. 18, 2020, which claims the benefit of European Application No. 19192044.6, filed Aug. 16, 2019, European Application No. 19192042.0, filed Aug. 16, 2019, International Application No. PCT/CN2019/093326, filed Jun. 27, 2019, and International Application No. PCT/CN2019/093275, filed Jun. 27, 2019, each of which is incorporated herein by reference.

FIELD

The present invention relates to novel monooxygenases which are useful in the hydroxylation of aromatic hydrocarbons. They are particularly useful for the production of 1-naththol and 7-hydroxycoumarin from naphthalene and 7-ethoxycoumarin, respectively.

BACKGROUND

Hydroxylated hydrocarbons, particularly 1-naththol and 7-hydroxycoumarin, are important raw materials in the chemical industry. Presently, said compounds are produced by purely chemical processes. The currently used chemical methods of producing 1-naphthol are mainly divided into three types. The most widely used method in large-scale production is based hydrogenation, oxidation and dehydrogenation of naphthalene. This method is characterized by high quality and continuous production, but low yield and the use of acids, bases, and metal catalysts. These compounds may be expensive or may cause environmental problems if not disposed of properly. Proper disposal may be an additional cost factor.

Biotechnological methods have become more popular for the synthesis of chemical compounds. Generally, such methods are characterized by mild reaction conditions, thus saving energy, and high specificity so that few undesired side products are formed. A P450 monooxygenase capable of introducing hydroxyl groups into a variety of aromatic hydrocarbons has been isolated from *Rhodococcus ruber* (Liu et al., 2006, Appl. Microbiol. Biotechnol. 72: 876-882). In principle, this enzyme opens the route to biotechnological methods for manufacturing hydroxylated aromatic hydrocarbons. However, the wild-type enzyme has a low catalytic activity which is not sufficient for an economically viable production process.

SUMMARY

The above-described problems are solved by the embodiments defined in the claims and in the description below.

DETAILED DESCRIPTION

In a first embodiment, the present invention relates to a modified P450 monooxygenase having an amino acid sequence as defined by SEQ ID NO: 1 or an amino acid sequence with at least 90% sequence identity with SEQ ID NO. 1, wherein the asparagine at position 199 or at the homologous position is substituted by an amino acid selected from the group consisting of glutamine, isoleucine, leucine phenylalanine, histidine, methionine, arginine, serine, threonine, tyrosine, tryptophan, alanine, valine and lysine, wherein said functional mutation leads to an improved reactivity on hydroxylation of aromatic hydrocarbons.

SEQ ID NO. 1 defines the amino acid sequence of a P450 monooxygenase isolated from *Rhodococcus ruber* DSM 44319. A "modified P450 monooxygenase" has an amino acid sequence which differs at least at amino acid position 199 from the amino acid sequence defined by SEQ ID NO. 1.

In addition to the sequence modifications set forth below in this application, the amino acid sequence of the modified P450 monooxygenase of the present invention may have further differences to the amino acid sequence of the wild-type enzyme as defined by SEQ ID NO. 1 provided that these sequence differences do not affect its function i.e. the improved reactivity on hydroxylation of aromatic carbons. It is well known to the person skilled in the art that not all parts of the amino acid sequence of an enzyme are equally important. Sequence regions which are not required for the catalytic function may in many cases be altered or even deleted without impairing the enzymatic activity of the protein.

Therefore, the present invention also relates to proteins having at least 90%, more preferably at least 95% and most preferably at least 98% sequence identity to the amino acid sequence defined by SEQ ID NO. 1, provided that such proteins still have an improved reactivity on the hydroxylation of aromatic hydrocarbons.

The person skilled in the art is aware that additions or deletions of amino acids to/from SEQ ID NO. 1 may shift the particular amino acids positions recited in this application. Therefore, any amino acid position referred to in this application based on the wild-type sequence must be understood as referring to the homologous amino acid position in a protein derived from SEQ ID NO. 1 by deleting or adding amino acids. These homologous positions can be determined using common methods of sequence alignment well known to the person skilled in the art.

Variants of SEQ ID NO. 1 having the degrees of sequence identity set forth above are preferably derived from SEQ ID NO. 1 only by conservative substitutions of amino acids. A "conservative substitution" is a substitution on one amino acid by a different amino acid with similar properties. Preferably, it is an exchange of an amino acid with a non-polar side chain for another amino acid with a non-polar side chain, an exchange of an amino acid with an acidic side chain for another amino acid with an acidic side chain, an amino acid with a basic side chain for another amino acid with a basic side chain or an exchange of an amino acid with a polar side chain for another amino acid with a polar side chain. Because the properties of the side chains in conservative substitutions do not change much, the overall structure of the resulting protein will not be severely affected.

Variants of SEQ ID NO. 1 derived from this sequence by addition of amino acids and having the degrees of sequence identity set forth above are, preferably, derived from SEQ ID NO. 1 by addition of up to 35, more preferably up to 20 and most preferably up to 10 amino acids at the C-terminus and/or the N-terminus. Typical additions to a protein are additions of amino acid sequences which make the purification of the expressed protein easier. One particularly preferred modification is the addition of several histidines, a so-called "his-tag". Also preferred is the addition of peptide linkers.

Variants of SEQ ID NO. 1 derived from this sequence by deletion of amino acids and having the degrees of sequence identity set forth above are, preferably, derived from SEQ ID NO. 1 by deletion of up to 35, more preferably up to 20 and most preferably up to 10 amino acids at the C-terminus and/or the N-terminus.

"Polar amino acids" or "amino acids with polar side chains" as understood by the present application are glycine, serine, threonine, cysteine, asparagine, glutamine, tryptophan and tyrosine.

"Non-polar amino acids" or "amino acids with polar side chains" as understood by the present application are alanine, valine, leucine, iso-leucine, phenylalanine, proline, and methionine.

Amino acids with acidic side chains as understood by the present application are aspartate and glutamic acid.

Amino acids with basic side chains as understood by the present application are lysine, arginine and histidine.

Single Substitutions

In a preferred embodiment of the present invention, the asparagine at position 199 of the P450 monooxygenase as defined by SEQ ID NO: 1 is substituted by an amino acid selected from the group consisting of glutamine, isoleucine, leucine phenylalanine, histidine, methionine, arginine, serine, tryptophan, alanine and valine. These modifications have a high catalytic activity for the hydroxylation of 7-ethoxycoumarin in addition to the hydroxylation of naphthalene.

In an especially preferred embodiment of the present invention, the asparagine at position 199 of the P450 monooxygenase as defined by SEQ ID NO: 1 is substituted by glutamine or isoleucine, most preferably glutamine. These are the modifications with a single substitution which show the highest catalytic activity for the hydroxylation of both naphthalene and 7-ethoxycoumarin.

The study underlying the present invention has shown that the P450 monooxygenases which carry one or two additional substitutions have an even higher catalytic activity.

Substitutions at Positions 88 and 199

Therefore, in a further preferred embodiment, the present invention relates to a modified P450 monooxygenase, wherein (i) asparagine at position 199 of the P450 monooxygenase as defined by SEQ ID NO: 1 is substituted by an amino acid selected from the group consisting of glutamine, isoleucine, leucine phenylalanine, histidine, methionine, arginine, serine, threonine, tyrosine, tryptophan, alanine, valine and lysine, and (ii) glutamic acid at position 88 is substituted by an amino acid selected from the group consisting of alanine, serine, histidine, threonine, cysteine, methionine and asparagine.

More preferably, glutamic acid at position 88 is substituted by an amino acid selected from the group consisting of alanine, serine, histidine, threonine, cysteine and methionine. With these substitutions, the catalytic activity of the enzyme with naphthalene as wells as 7-ethoxycoumarin is increased. Most preferably glutamic acid at position 88 is substituted by an amino acid selected from the group consisting of alanine, cysteine and methionine.

In an even more preferred further embodiment of the present invention, (i) asparagine at position 199 of the P450 monooxygenase defined by SEQ ID NO: 1 is substituted by an amino acid selected from the group consisting of glutamine, isoleucine, leucine phenylalanine, histidine, methionine, arginine, serine, tryptophan, alanine and valine, and (ii) glutamic acid at position 88 is substituted by an amino acid selected from the group consisting of alanine, serine, histidine, threonine, cysteine, methionine and asparagine.

More preferably, glutamic acid at position 88 is substituted by an amino acid selected from the group consisting of alanine, serine, histidine, threonine, cysteine and methionine. With these substitutions, the catalytic activity of the enzyme with naphthalene as wells as 7-ethoxycoumarin is increased. Most preferably glutamic acid at position 88 is substituted by an amino acid selected from the group consisting of alanine, cysteine and methionine.

The most preferred combination of substitutions at positions 88 and 199 is the combination of alanine or cysteine at position 88 with glutamine at position 199.

Substitutions at Positions 199 and 209

And in yet another preferred embodiment, the present invention relates to a modified P450 monooxygenase, wherein (i) asparagine at position 199 of the P450 monooxygenase defined by SEQ ID NO: 1 is substituted by an amino acid selected from the group consisting of glutamine, isoleucine, leucine phenylalanine, histidine, methionine, arginine, serine, threonine, tyrosine, tryptophan, alanine, valine and lysine, and (ii) glutamine at position 209 is substituted by alanine.

In an even more preferred further embodiment of the present invention, (i) asparagine at position 199 of the P450 monooxygenase defined by SEQ ID NO: 1 is substituted by an amino acid selected from the group consisting of glutamine, isoleucine, leucine phenylalanine, histidine, methionine, arginine, serine, tryptophan, alanine and valine, and (ii) glutamine at position 209 is substituted by alanine.

The most preferred combination of substitutions at positions 199 and 209 is the combination of glutamine at position 199 and alanine at position 209.

Triple Substitutions

In the most preferred embodiment of a modified P450 monooxygenase (i) asparagine at position 199 of the P450 monooxygenase defined by SEQ ID NO: 1 is substituted by an amino acid selected from the group consisting of glutamine, isoleucine, leucine phenylalanine, histidine, methionine, arginine, serine, threonine, tyrosine, tryptophan, alanine, valine and lysine, (ii) glutamic acid at position 88 is substituted by an amino acid selected from the group consisting of alanine, serine, histidine, threonine, cysteine, methionine and asparagine.

More preferably, glutamic acid at position 88 is substituted by an amino acid selected from the group consisting of alanine, serine, histidine, threonine, cysteine and methionine. With these substitutions, the catalytic activity of the enzyme with naphthalene as wells as 7-ethoxycoumarin is increased. Most preferably glutamic acid at position 88 is substituted by an amino acid selected from the group consisting of alanine, cysteine and methionine, and (iii) glutamine at position 209 is substituted by alanine.

It is even more preferred that (i) asparagine at position 199 of the P450 monooxygenase defined by SEQ ID NO: 1 is substituted by an amino acid selected from the group consisting of glutamine, isoleucine, leucine phenylalanine, histidine, methionine, arginine, serine, tryptophan, alanine and valine, (ii) glutamic acid at position 88 is substituted by an amino acid selected from the group consisting of alanine, cysteine and methionine and (iii) glutamine at position 209 is substituted by alanine.

A particularly preferred combination of substitutions at positions 199, 88 and 209 is glutamine at position 199, alanine or cysteine, most preferably cysteine, at position 88 and alanine at position 209.

Reactivity with Hydrocarbons

The term "reactivity with hydrocarbons" refers to the enzyme's ability to catalyze the introduction of an hydroxyl group into a hydrocarbon compound selected from the group consisting of naphthalene, 7-ethoxycoumarin, acenaphthene, fluorine, indene, toluene, ethylbenzene and m-xylene. Preferably, the modified P450 monooxygenase of the present invention has an improved reactivity on hydroxylation of naphthalene and/or 7-ethoxycoumarin.

The reaction products resulting from hydroxylation of the aforementioned substrates with the P450 monooxygenase of the present invention can be found below:

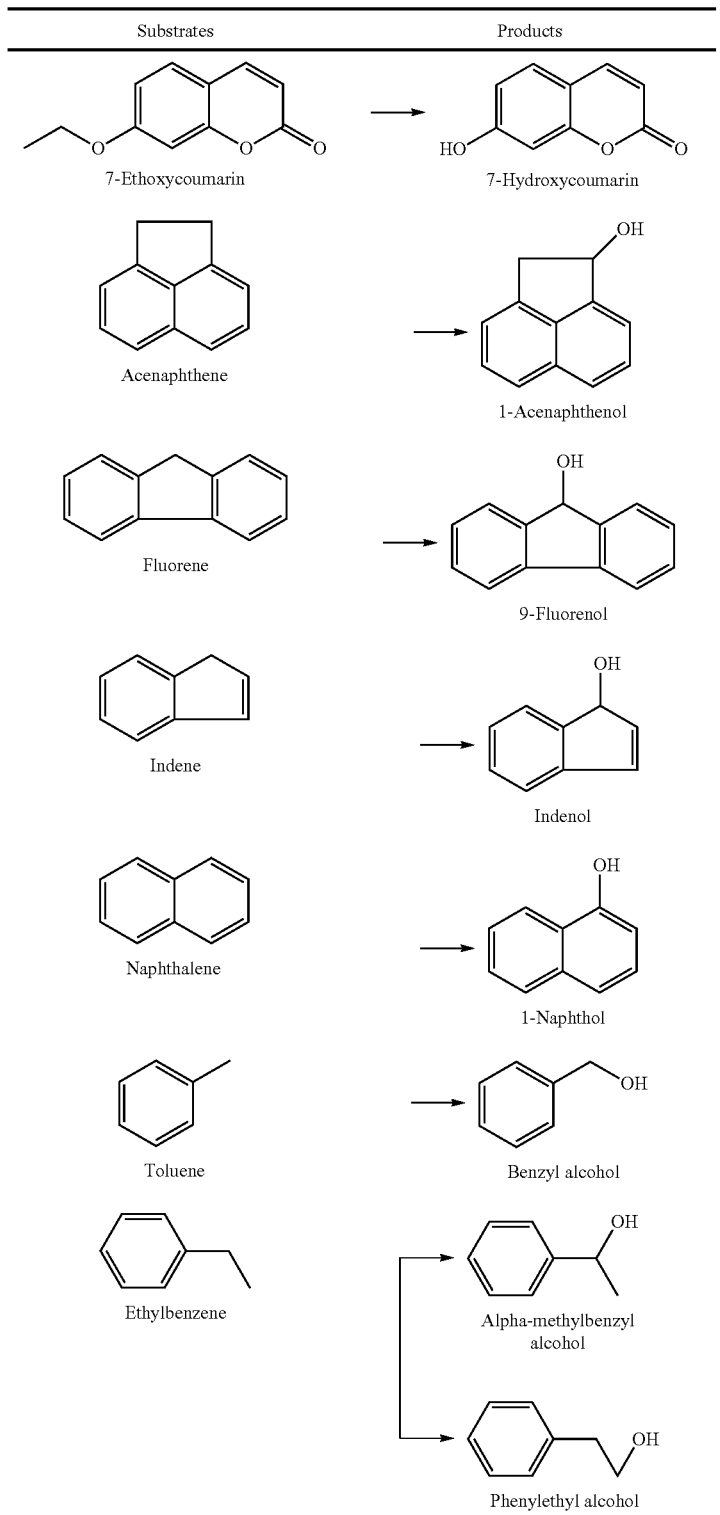

| Substrates | Products |
|---|---|
| 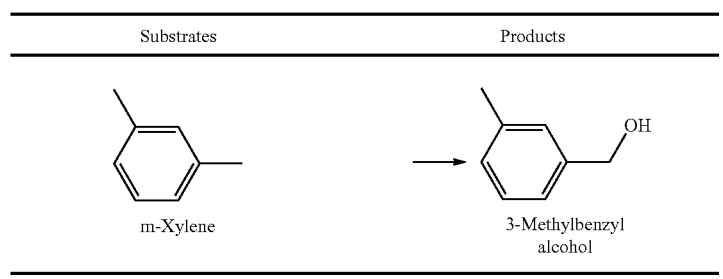 | |
| m-Xylene | 3-Methylbenzyl alcohol |

The reactivity on hydroxylation of aromatic carbons is, preferably, determined in phosphate-buffered saline solution (PBS) with 0.15 g/l of the hydrocarbon to be tested. The hydrocarbon is, preferably, taken from a 3 g/l stock solution in DMSO. The preferred incubation time at 30° C. is 2 hours. The products are then extracted with methyl-tert butyl ether and analyzed by HPLC, preferably using a C18 reverse-phase column. An enzyme shows "improved reactivity" towards the hydrocarbon in question of its specific activity in the above-described assay is higher than that of the wild-type enzyme defined by SEQ ID NO. 1. Preferably, the specific activity is determined using equal concentrations of a purified enzyme. However, a whole-cell assay as described in the examples may also be used.

In another embodiment, the present invention relates to nucleic acid sequence encoding any of the modified P450 monooxygenases defined above. The invention also relates nucleic acid sequences having a complementary sequence to the aforementioned nucleic acid sequence.

In yet another embodiment, the present invention relates to an expression construct, comprising the nucleic acid sequence of claim 5 as defined above under the genetic control of a regulatory nucleic acid sequence.

The term "expression construct" is well known to the person skilled in the art. An "expression construct" is a nucleic acid molecule comprising a protein coding region and a regulatory sequence which enables the transcription of the protein coding region. Suitable regulatory sequences depend on the host cell which is intended to be used for the recombinant expression of the protein. The person skilled in the art is able to select suitable regulatory regions based on his common knowledge about transcription processes in the selected host cell. A preferred expression construct for the recombinant expression of a modified P450 monooxygenase according to the present invention in *E. coli* has a nucleic acid sequence as defined by SEQ ID NO. 2

In yet another embodiment, the present invention relates to a vector, comprising the nucleic acid as defined above or the expression construct as defined above.

The term "vector" is well known to the person skilled in the art. It is a nucleic acid sequence which can be replicated in a host cell. Hence, it must comprise all genetic elements which are required for successful replication in the selected host cell. The person skilled in the art knows which vectors to use for a specific host cell.

In yet another embodiment, the present invention relates to a microorganism comprising the nucleic acid as defined above or the expression construct as defined above or the vector as defined above.

In principle, any microorganism which allows the recombinant expression of transgenes may be used. Thus, the suitable microorganism is one, for which regulatory elements as defined above are known and for which vectors as defined above may be constructed. Preferably, the microorganism is a prokaryote, more preferably a bacterium, or a yeast. Preferred bacteria belong to the genera *Rhodococcus* or *Escherichia*. A preferred yeast is *Pichia pastoris*. The microorganism is, most preferably, *E. coli, R. ruber* or *Pichia pastoris*.

In yet another embodiment, the present invention relates to a method for producing the modified p450 monooxygenase as defined above in this application comprising the step of incubating the recombinant microorganism as defined above under conditions suitable for the expression of the monooxygenase.

The person skilled in the art knows that different microorganisms have different requirements with regard to the composition of the medium, energy and carbon sources as well as temperature and oxygen supply. He is well able to select suitable conditions based on his knowledge of microbial physiology. If an inducible promotor is used as regulatory element in the expression construct, the person skilled in the knows the conditions required for the induction of translation.

In yet another embodiment, the present invention relates to a method for the hydroxylation of an aromatic hydrocarbon, comprising the step of
 a1) having at least one of the modified P450 monooxygenases according to the present invention mixed and reacted with said aromatic hydrocarbon and having said aromatic hydrocarbon thus hydroxylated; or
 a2) having at least one of the recombinant microorganisms as defined above mixed and reacted with said aromatic hydrocarbon.

The person skilled in the art is able to find suitable reaction conditions by simple experiments. The preferred reaction temperature is 30° C. The preferred pH is 7.4. Preferably, the reaction takes place in the presence of potassium ions (25 mM). The preferred substrate concentration is 0.12 g/L. If whole bacterial cells are used (embodiment a2), the $OD_{600}$ should be 30. The person skilled in the art is well aware that the enzyme retains at least some activity in conditions which deviate in one or more parameters from the conditions given above. Hence, the method of the present invention is not limited to those parameters and the particular parameters disclosed above provide only one of several embodiments of the invention. Using the methods disclosed in the present application, the person skilled in the art can easily test the enzyme's activity under different reaction conditions.

If the method according to a2) is used it is preferred that the microorganism has been incubated under conditions suitable for the expression of the modified P450 monooxygenase before mixing it with said aromatic hydrocarbon. It is also preferred to wash this microorganism in a suitable buffer before mixing it with aromatic hydrocarbon in order to limit the presence of undesired side products.

All definitions pertaining to the modified P450 monooxygenases of the present invention, suitable hydrocarbons and host cells given further above in this application also apply to this embodiment.

In yet another embodiment, the present invention relates to the use of the modified P450 monooxygenase according to the present invention for the hydroxylation of an aromatic carbon.

The following examples are only intended to illustrate the invention. They shall not limit the scope of the claims in any way.

All definitions given above also apply to this embodiment.

EXAMPLES

Construction of Nucleic Acids Encoding Modified P450 Monooxygenases

A full-length gene encoding P450 protein was synthesized and amplified by PCR using the following primers: 5-ctg GAATTCATGAGTGCATCAGTTCCGGCGT-3' (SEQ ID NO: 3) and 5-catcAAGCTTTCAGAGTCGCAGGGCCA-3' (SEQ ID NO: 4). The EcoRI and HindIII restriction endonuclease sites in the primer sequences are underlined. The PCR product was isolated and digested with EcoRI and HindIII restriction endonucleases, cloned into the pET28a (+) vector, and expressed in *E. coli* BL21(DE3) cells. The sequence of the insert DNA was subsequently confirmed by sequencing.

Mutagenesis was performed as generally known in the art by designing suitable primers and conducting whole plasmid PCR. Thereafter, the original plasmid was digested by DpnI.

Recombinant Expression of Modified P450 Monooxygenases

*E. coli* BL21 (DE3) containing the expression construct was grown in 100 mL Luria-Bertani medium, supplemented with 50 µg ml$^{-1}$ kanamycin, at 37° C. and 120 rpm. Expression was induced with 0.25 mM isopropyl-β-D-thiogalactopyranoside (IPTG) and cells were incubated for 24 h at 18° C. Cells were harvested by centrifugation (~10,000×g), washed with phosphate-buffered saline (PBS) and resuspended into PBS. The cell final concentration was adjusted to OD$_{600}$ 20 before the reaction.

Assessment of the Activity of Recombinant P450 Monooxygenases

The whole-cell reaction was initiated by adding 0.15 g/L PAH from a 3 g/L stock in DMSO to 2 mL working volume in a 10 mL vial. After 2 h, the products were extracted with 2 mL methyl tert-butyl ether (MTBE) after vigorous vortexing for 5 min. After centrifugation, the organic phase was transferred to a fresh glass tube and evaporated to dryness. The remaining residue was resolubilized with methanol. Samples were quantified by HPLC using an Alltech series 1500 instrument equipped with a prevail C18 reverse-phase column maintained at 25° C. For detection, 50% methanol was applied as the mobile phase at a flow rate of 1.0 mL min$^{-1}$. Products were detected by monitoring the absorbance at 272 nm.

TABLE 1

Effects of substitution of different amino acids by alanine on enzyme activity

| Mutants | 1-Naphthol production (mg · L$^{-4}$ · h$^{-1}$) | 7-Hydroxycoumarin production (mg · L$^{-1}$ · h$^{-1}$) |
|---|---|---|
| Wild-type | 0.51 ± 0.05 | 46.98 ± 3.40 |
| L87A | 0.23 ± 0.05 | 48.44 ± 1.78 |
| E88A | 0.99 ± 0.04 | 153.98 ± 1.14 |
| K89A | 0.55 ± 0.02 | 96.31 ± 4.72 |
| I90A | 0.65 ± 0.08 | 58.31 ± 3.07 |
| T91A | 0.54 ± 0.12 | 44.98 ± 4.16 |
| P92A | 0.49 ± 0.09 | 49.02 ± 3.07 |
| V93A | 0.20 ± 0.10 | 28.71 ± 4.16 |
| S94A | 0.52 ± 0.05 | 48.14 ± 3.18 |
| E95A | 0.82 ± 0.11 | 62.42 ± 0.46 |
| E96A | 0.56 ± 0.06 | 71.52 ± 4.46 |
| T98A | 0.26 ± 0.05 | 39.84 ± 2.37 |
| T100A | 0.65 ± 0.09 | 86.75 ± 4.00 |
| L101A | 0.68 ± 0.03 | 120.58 ± 3.78 |
| R103A | 0.45 ± 0.10 | 76.82 ± 4.29 |
| Y104A | 0.19 ± 0.01 | 35.74 ± 2.96 |
| D105A | 0.41 ± 0.13 | 36.46 ± 4.14 |
| H196A | 0.54 ± 0.05 | 46.16 ± 3.96 |
| T197A | 0.71 ± 0.08 | 48.43 ± 2.91 |
| V198A | 0.08 ± 0.04 | 38.70 ± 0.57 |
| N199A | 1.73 ± 0.01 | 134.04 ± 2.54 |
| T200A | 0.44 ± 0.04 | 46.72 ± 3.15 |
| W201A | 0.35 ± 0.12 | 33.79 ± 2.38 |
| G202A | 0.37 ± 0.10 | 35.65 ± 1.12 |
| R203A | 1.28 ± 0.04 | 144.63 ± 5.60 |
| P204A | 0.66 ± 0.07 | 182.97 ± 9.32 |
| P206A | 0.29 ± 0.13 | 39.31 ± 0.85 |
| E207A | 0.58 ± 0.05 | 62.62 ± 5.67 |
| E208A | 0.37 ± 0.04 | 24.84 ± 1.56 |
| Q209A | 1.90 ± 0.07 | 225.27 ± 3.04 |
| V210A | 0.49 ± 0.02 | 43.92 ± 2.93 |

TABLE 2

Effect of substitutions at amino acid position 88 on enzyme activity

| Mutants | 1-Naphthol production (mg · L$^{-4}$ · h$^{-1}$) | 7-Hydroxycoumarin production (mg · L$^{-1}$ · h$^{-1}$) |
|---|---|---|
| Wild-type | 0.51 ± 0.05 | 46.98 ± 3.4 |
| E88A | 0.99 ± 0.04 | 153.98 ± 1.14 |
| E88D | 0.49 ± 0.03 | 62.52 ± 2.13 |
| E88S | 0.86 ± 0.02 | 77.44 ± 2.29 |
| E88H | 0.81 ± 0.05 | 121.15 ± 4.87 |
| E88G | 0.31 ± 0.08 | 38.12 ± 1.34 |
| E88R | 0.37 ± 0.03 | 61.69 ± 9.31 |
| E88T | 0.79 ± 0.05 | 102.78 ± 12.02 |
| E88P | 0 | 3.8 ± 0.63 |
| E88C | 1.05 ± 0.05 | 126.38 ± 1.48 |
| E88Y | 0.43 ± 0.11 | 71.18 ± 3.07 |
| E88V | 0.51 ± 0.05 | 44.33 ± 2.33 |
| E88M | 0.95 ± 0.03 | 120.87 ± 22.18 |
| E88K | 0.71 ± 0.08 | 77.55 ± 5.89 |
| E88I | 0.48 ± 0.09 | 37.52 ± 13.85 |
| E88L | 0.75 ± 0.05 | 86.15 ± 1.23 |
| E88F | 0.06 ± 0.02 | 11.14 ± 0.61 |
| E88N | 0.61 ± 0.07 | 112.95 ± 0.84 |
| E88Q | 0.46 ± 0.02 | 51.49 ± 1.88 |
| E88W | 0.09 ± 0.02 | 26.27 ± 1.29 |

TABLE 3

Effect of substitutions at amino acid position 199 on enzyme activity

| Mutants | 1-Naphthol production (mg · L$^{-4}$ · h$^{-1}$) | 7-Hydroxycoumarin production (mg · L$^{-1}$ · h$^{-1}$) |
|---|---|---|
| Wild-type | 0.51 ± 0.05 | 46.98 ± 3.4 |
| N199A | 1.73 ± 0.01 | 134.04 ± 2.54 |
| N199D | 0 | 28.95 ± 1.68 |
| N199S | 2.66 ± 0.03 | 193.47 ± 15.83 |
| N199H | 3.46 ± 0.79 | 191.55 ± 1.71 |
| N199G | 0.34 ± 0.07 | 60.29 ± 6 |
| N199R | 3.22 ± 0.44 | 178.73 ± 3.93 |
| N199T | 2.48 ± 0.06 | 86.71 ± 1.99 |
| N199P | 2.71 ± 0.58 | 65.09 ± 3.2 |
| N199C | 0.42 ± 0.11 | 61.59 ± 6.89 |
| N199Y | 2.49 ± 0.08 | 263.26 ± 9.77 |
| 1N99V | 1.21 ± 0.43 | 135.94 ± 0.31 |
| N199M | 3.5 ± 0.3 | 150.44 ± 5.63 |
| N199K | 1.11 ± 0.18 | 66.55 ± 5.05 |
| N199I | 4.51 ± 0.37 | 212.94 ± 15.9 |
| N199L | 3.95 ± 0.26 | 267.08 ± 27 |
| N199F | 4.02 ± 0.18 | 217.51 ± 9.95 |
| N199Q | 6.64 ± 0.59 | 303.72 ± 39.38 |
| N199E | 3.21 ± 0.98 | 119.34 ± 14.43 |
| N199W | 2.69 ± 0.18 | 168.17 ± 12.37 |

TABLE 4

Effect of substitutions of multiple amino acids on enzyme activity

| Mutants | 1-Naphthol production (mg · L$^{-4}$ · h$^{-1}$) | 7-Hydroxycoumarin production (mg · L$^{-1}$ · h$^{-1}$) |
|---|---|---|
| Wild-type | 0.51 ± 0.05 | 46.98 ± 3.4 |
| CMA | 6.59 ± 0.45 | 134.67 ± 4.39 |
| CMB | 7 ± 0.51 | 149.91 ± 2.39 |
| CMC | 1.99 ± 0.15 | 73.48 ± 1.11 |
| CMABC | 7.19 ± 0.11 | 160.53 ± 5.05 |

CMA: E88C/N199Q
CMB: N199Q/Q209A
CMC: E88C/Q209A
CMABC: E88C/N199Q/Q209A

---

The invention claimed is:

1. A modified P450 monooxygenase having an amino acid sequence with at least 90% sequence identity with SEQ ID NO: 1, wherein the asparagine at position 199 of the amino acid sequence of SEQ ID NO. 1 is substituted by an amino acid selected from the group consisting of glutamine, isoleucine, leucine, phenylalanine, histidine, methionine, arginine, serine, threonine, tyrosine, tryptophan, alanine, valine, and lysine to provide a functional mutation, wherein said functional mutation leads to an improved reactivity on hydroxylation of aromatic hydrocarbons as compared to a non-modified P450 monooxygenase.

2. The modified P450 monooxygenase of claim 1, wherein the asparagine at position 199 is substituted by an amino acid selected from the group consisting of glutamine, isoleucine, leucine, phenylalanine, histidine, methionine, arginine, serine, tryptophan, alanine, and valine.

3. The modified P450 monooxygenase of claim 2, wherein the asparagine at position 199 is substituted by glutamine or isoleucine.

4. The modified P450 monooxygenase according to claim 1, wherein additionally
   a) glutamic acid at position 88 is substituted by an amino acid selected from the group consisting of alanine, serine, histidine, threonine, cysteine, methionine, and asparagine, and/or
   b) glutamine at position 209 is substituted by alanine.

5. The modified P450 monooxygenase according to claim 1, wherein the sequence having at least 90% sequence identity with the sequence defined by SEQ ID NO. 1 comprises one or more conservative substitutions of amino acids as compared to the amino acid sequence defined by SEQ ID NO. 1.

6. The modified P450 monooxygenase according to claim 1, having an addition of up to 35 amino acids at the N-terminus and/or the C-terminus.

7. The modified P450 monooxygenase according to claim 1, having a deletion of up to 35 amino acids at the N-terminus and/or the C-terminus.

8. The modified P450 monooxygenase according to claim 1, wherein the improved reactivity on hydroxylation of aromatic hydrocarbons comprises an increased activity on at least one hydrocarbon selected from the group consisting of naphthalene, 7-ethoxy-hydroxycoumarin, acenaphthene, fluorene, indene, methylbenzene, and ethylbenzene as compared to a non-modified P450 monooxygenase.

9. A method for the hydroxylation of an aromatic hydrocarbon, comprising
   a1) having at least one of the modified P450 monooxygenases according to claim 1 mixed and reacted with said aromatic hydrocarbon and having said aromatic hydrocarbon thus hydroxylated; or
   a2) having a recombinant microorganism expressing the modified P450 monooxygenase according to claim 1 mixed and reacted with said aromatic hydrocarbon.

10. The method according to claim 9, wherein the aromatic hydrocarbon is selected from the group consisting of naphthalene, 7-ethoxy-hydroxycoumarin, acenaphthene, fluorene, indene, methylbenzene, ethylbenzene, and mixtures thereof.

11. The method according to claim 9, wherein the hydroxylated aromatic hydrocarbon is selected from the group consisting of 1-naphthol, 7-hydroxycoumarin, 1-acenaphthylene, 9-benflumetol, indenol, benzyl alcohol, 3-methylbenzyl alcohol, and mixtures thereof.

\* \* \* \* \*